US011674838B2

(12) United States Patent
Brewer et al.

(10) Patent No.: US 11,674,838 B2
(45) Date of Patent: Jun. 13, 2023

(54) CAPACITIVE FRINGE FIELD OIL LEVEL SENSOR WITH INTEGRATED HUMIDITY AND TEMPERATURE SENSING

(71) Applicant: Poseidon Systems, LLC, Rochester, NY (US)

(72) Inventors: Ryan C. Brewer, Webster, NY (US); Zachary M. Allen, Winthrop, ME (US); Timothy R. Marvin, Rochester, NY (US); Matthew Anauo, Elba, NY (US)

(73) Assignee: Poseidon Systems LLC, Rochester, NY (US)

( * ) Notice: Subject to any disclaimer, the term of this patent is extended or adjusted under 35 U.S.C. 154(b) by 127 days.

(21) Appl. No.: 16/839,521

(22) Filed: Apr. 3, 2020

(65) Prior Publication Data
US 2020/0319011 A1    Oct. 8, 2020

Related U.S. Application Data

(60) Provisional application No. 62/829,069, filed on Apr. 4, 2019.

(51) Int. Cl.
*G01F 23/26* (2022.01)
*G01N 33/28* (2006.01)
*G01N 27/22* (2006.01)

(52) U.S. Cl.
CPC .......... *G01F 23/26* (2013.01); *G01N 27/221* (2013.01); *G01N 33/2847* (2013.01)

(58) Field of Classification Search
CPC ... G01F 23/26; G01N 27/221; G01N 33/2847

USPC ......................................... 73/53.05
See application file for complete search history.

(56) References Cited

U.S. PATENT DOCUMENTS

| | | | |
|---|---|---|---|
| 3,580,074 A | 5/1971 | Wescott et al. | |
| 4,083,248 A | 4/1978 | Maier | |
| 4,780,705 A | 10/1988 | Beane | |
| 4,795,967 A | 1/1989 | Fredericks | |
| 4,806,847 A | 2/1989 | Atherton et al. | |
| 4,841,227 A | 6/1989 | Maier | |
| 4,864,857 A | 9/1989 | Koon | |
| 4,888,989 A | 12/1989 | Homer | |
| 4,947,689 A | 8/1990 | Hochstein | |

(Continued)

FOREIGN PATENT DOCUMENTS

| | | |
|---|---|---|
| CN | 101561307 | 10/2009 |
| DE | 19516809 | 9/1996 |

(Continued)

OTHER PUBLICATIONS

English Translation of Chinese Patent CN101561307. Oct. 21, 2009.

(Continued)

*Primary Examiner* — David Z Huang
*Assistant Examiner* — Jean F Morello
(74) *Attorney, Agent, or Firm* — Duane C. Basch; Dawson Law Firm, PC (57) ABSTRACT

A sensor for measuring multiple properties of a fluid, such as oil, including level, temperature, water contamination, and dielectric where the sensing elements include two or more interdigitated electrodes, a capacitive relative humidity sensor, and a temperature sensing element.

24 Claims, 6 Drawing Sheets

(56) References Cited

U.S. PATENT DOCUMENTS

| | | | |
|---|---|---|---|
| 4,982,606 | A | 1/1991 | Adamski et al. |
| 4,987,776 | A | 1/1991 | Koon |
| 5,005,407 | A | 4/1991 | Koon |
| 5,005,409 | A | 4/1991 | Hochstein |
| 5,051,921 | A | 9/1991 | Paglione |
| 5,103,368 | A | 4/1992 | Hart |
| 5,121,631 | A | 6/1992 | Koon |
| 5,182,545 | A | 1/1993 | Goekler et al. |
| 5,243,860 | A | 9/1993 | Habart |
| 5,304,347 | A | 4/1994 | Mann et al. |
| 5,331,287 | A * | 7/1994 | Yamagishi .......... G01N 33/2888 340/603 |
| 5,365,783 | A | 11/1994 | Zweifel |
| 5,406,843 | A | 4/1995 | Hannan et al. |
| 5,437,184 | A | 8/1995 | Shillady |
| 5,495,745 | A | 3/1996 | Hughes |
| 5,532,527 | A | 7/1996 | Zatler et al. |
| 5,540,086 | A * | 7/1996 | Park ................... G01N 33/2888 73/54.01 |
| 5,546,005 | A | 8/1996 | Rauchwerger |
| 5,602,333 | A | 2/1997 | Larrebee et al. |
| 5,613,399 | A | 3/1997 | Hannan et al. |
| 5,722,290 | A | 3/1998 | Kronberg |
| 5,726,908 | A | 3/1998 | Hosmer et al. |
| 5,745,377 | A | 4/1998 | Power et al. |
| 5,790,422 | A | 8/1998 | Power et al. |
| 5,802,728 | A | 9/1998 | Karnick et al. |
| 5,860,316 | A | 1/1999 | Berrill |
| 5,861,811 | A * | 1/1999 | Lease ................... G01F 23/265 73/304 C |
| 5,973,415 | A | 10/1999 | Brenner et al. |
| 6,016,697 | A | 1/2000 | McCulloch et al. |
| 6,073,488 | A | 6/2000 | Byatt et al. |
| 6,125,696 | A | 10/2000 | Hannan et al. |
| 6,138,508 | A | 10/2000 | Hannan et al. |
| 6,148,666 | A | 11/2000 | Roesicke |
| 6,240,778 | B1 | 6/2001 | Hannan et al. |
| 6,490,920 | B1 * | 12/2002 | Netzer ................. G01C 9/06 324/687 |
| 6,539,797 | B2 | 4/2003 | Livingston et al. |
| 6,546,975 | B1 | 4/2003 | Dietz |
| 6,551,558 | B1 | 4/2003 | Mann et al. |
| 6,578,416 | B1 | 6/2003 | Vogel et al. |
| 6,617,968 | B1 * | 9/2003 | Odisho ................ F16N 29/00 340/438 |
| 6,658,929 | B2 | 12/2003 | Atkinson |
| 6,809,528 | B1 * | 10/2004 | Stormbom ............ G01N 25/56 324/664 |
| 6,857,313 | B2 | 2/2005 | Williamson |
| 6,943,566 | B2 | 9/2005 | Florin et al. |
| 7,005,864 | B2 * | 2/2006 | Iannello ................ G01D 3/02 324/632 |
| 7,222,526 | B2 | 5/2007 | Baker et al. |
| 7,240,690 | B2 | 7/2007 | Schmitz et al. |
| 7,373,817 | B2 | 5/2008 | Burdi et al. |
| 7,487,793 | B2 | 2/2009 | Schmitz et al. |
| 7,600,424 | B2 | 10/2009 | Sasaki et al. |
| 7,665,358 | B2 | 2/2010 | Calabrese |
| 7,730,780 | B2 | 6/2010 | Neven et al. |
| 7,779,858 | B2 | 8/2010 | Schmitz et al. |
| 7,802,471 | B2 | 9/2010 | Sieh et al. |
| 7,814,787 | B2 * | 10/2010 | Sabini ................... G01F 23/02 73/304 C |
| 7,823,447 | B2 | 11/2010 | Harazin et al. |
| 7,895,891 | B2 | 3/2011 | Prieto Barranco et al. |
| 8,024,967 | B2 | 9/2011 | Burdi et al. |
| 8,181,516 | B2 | 5/2012 | Naydenov |
| 8,291,761 | B2 | 10/2012 | Burdi et al. |
| 8,380,355 | B2 | 2/2013 | Mayleben et al. |
| 8,474,315 | B2 | 7/2013 | Ohshima et al. |
| 8,783,454 | B2 | 7/2014 | Camenisch et al. |
| 8,810,280 | B2 | 8/2014 | Zhou |
| 8,844,351 | B2 | 9/2014 | Burdi et al. |
| 9,109,940 | B2 | 8/2015 | Bahorich et al. |
| 9,153,119 | B2 | 10/2015 | Stapleford |
| 9,429,461 | B2 | 8/2016 | Gebhardt et al. |
| 9,599,501 | B2 | 3/2017 | Kokawa |
| 9,604,043 | B2 | 3/2017 | King |
| 9,718,549 | B2 | 8/2017 | Hennings et al. |
| 9,733,116 | B2 | 8/2017 | Hoppe et al. |
| 9,752,914 | B2 | 9/2017 | Levine |
| 10,564,025 | B2 * | 2/2020 | Oldfield ................ G01F 23/268 |
| 2010/0294021 | A1 * | 11/2010 | Makino ................ G01N 25/18 73/204.11 |
| 2011/0000309 | A1 | 1/2011 | Griffiths et al. |
| 2011/0110794 | A1 | 5/2011 | Mayleben et al. |
| 2011/0120219 | A1 * | 5/2011 | Barlesi ................. G01F 23/266 73/304 C |
| 2011/0265562 | A1 | 11/2011 | Li |
| 2014/0266065 | A1 * | 9/2014 | Von Herzen ....... G01N 33/2888 320/167 |
| 2014/0318236 | A1 * | 10/2014 | Lingle ................... G01F 23/26 73/290 R |
| 2015/0122015 | A1 | 5/2015 | Leppard |
| 2015/0338326 | A1 * | 11/2015 | Campbell ............ F16C 19/52 73/781 |
| 2017/0191861 | A1 | 7/2017 | Rondano et al. |
| 2017/0219413 | A1 | 8/2017 | Kokawa |
| 2020/0072651 | A1 * | 3/2020 | Tadas ................... G01F 23/268 |

FOREIGN PATENT DOCUMENTS

| | | |
|---|---|---|
| DE | 19645970 | 5/1998 |
| DE | 19728280 | 5/1998 |
| WO | 2010133067 | 11/2010 |

OTHER PUBLICATIONS

English Translation of German Patent DE19516809. Sep. 5, 1996.
English Translation of German Patent DE 19645970. May 14, 1998.
English Translation of German Patent DE19728280. May 28, 1998.

* cited by examiner

CAPACITIVE FRINGE FIELD OIL LEVEL SENSOR WITH INTEGRATED HUMIDITY AND TEMPERATURE SENSING

This application claims priority under 35 U.S.C. § 119(e) to U.S. Provisional Patent Application No. 62/829,069 for a CAPACITIVE FRINGE FIELD OIL LEVEL SENSOR WITH INTEGRATED HUMIDITY AND TEMPERATURE SENSING, filed Apr. 4, 2019 by Ryan C. Brewer, et al., which is hereby incorporated by reference in its entirety.

A sensor suitable for measuring multiple properties of a fluid including level, temperature, water contamination, and dielectric is described. The sensor may be used with lubricating and non-lubricating fluids (e.g., oils and emulsions thereof, cutting fluids and coolants, transformer oils and dielectric coolants, etc.). The sensor consists of at least the following: sensing elements, sensor interface electronics, processing and communications electronics, and a mechanical enclosure. In one embodiment, the sensing elements include two or more pairs of interdigitated electrodes, a capacitive relative humidity (RH) sensor, and a temperature sensing element. Level and dielectric signals (measurements) are provided by the interdigitated electrodes, water contamination data is provided by the capacitive relative humidity sensor, and temperature data is provided by a temperature sensing element.

BACKGROUND AND SUMMARY

Capacitive sensors are known to indicate when a petroleum-based liquid is at a certain level, for example, U.S. Pat. No. 4,780,705. Such sensors may include a sensing capacitor for monitoring changing capacitance in response to varying liquid level. Optionally included is a reference capacitor. The sensor includes a positive voltage source and a bridge circuit having two arms connected at a common input juncture to the voltage source and with a first of the arms including the sensing capacitor and the second of the arms including the reference capacitor. A comparator is responsive to the outputs of the arms to sense the differential therebetween and to continuously produce the positive sensor signal when the capacitance of the sensing capacitor increases from the predetermined capacitance. As suggested by the '705 patent, use of a capacitance sensor that is temperature and voltage compensative is also known.

In the measurement or monitoring of oil levels, a sensing technique may be based on sensing changes in a dielectric characteristic in the fluid surrounding interdigitated sensing elements. Lubricating oils typically have dielectric constants (e.g., quantification of the ability of a substance to store electrical energy in an electric field) between 2.0 and 2.5, while air has a dielectric constant near 1.0. Notably, the dielectric constant is typically expressed as the ratio of the permittivity of a substance (oil) to the permittivity of free space (air). This difference in the dielectric constant of oil to that of air is significant enough to cause an observable change in the capacitance of interdigitated electrodes exposed to oil versus air by a measurable and repeatable amount. To measure the dielectric, the sensor electronics drive an alternating voltage through the electrodes, which results in an alternating electric field extending into the oil orthogonal to the geometric plane of the electrodes. The capacitance of the electrodes changes based on the dielectric of the fluid covering the two electrodes of an interdigitated electrode pair, which the electric field passes through. Detecting or sensing the changing capacitance allows for determination of fluid level as well as fluid dielectric monitoring.

Disclosed in embodiments herein is a capacitive fringe field fluid (oil) level sensor, comprising: at least a first pair of interdigitated oil reference electrodes, said oil reference electrodes are placed at a position normally submerged in all but a severe low-oil condition; at least one pair of interdigitated measurement (monitoring) electrodes are spaced apart from the reference electrodes and from one another, so as to enable the monitoring of oil at one or more levels; optionally at least one pair of interdigitated air reference electrodes, may be placed at a position normally exposed to air; electronic circuitry, operatively connected to both the reference electrodes and the measurement electrodes, for applying an excitation voltage and monitoring the response of the reference electrodes and the measurement electrodes; a temperature sensor, located in proximity to the oil reference electrodes; a water contamination (RH) sensor, also referred to as a water activity sensor, suitable for characterizing the amount of water present in the oil, the water sensor employing a capacitive sensing element with a hygroscopic material between two electrodes of a capacitor, such that the dielectric constant of the material, as measured by the capacitance, changes as a function of the amount of water absorbed by the hygroscopic material, thereby producing a signal indicative of a relative level of water in the oil; and a microcontroller for the collection, storage and processing of signals to/from the electronic circuitry, the temperature sensor and the water sensor and for at least preliminary interrogation of such signals for the monitoring of one or more of the oil level, oil temperature, water contamination, and oil dielectric conditions. Such a system is, therefore, able to sense and measure multiple fluid conditions concurrently.

The various embodiments described herein are not intended to limit the disclosure to those embodiments described. On the contrary, the intent is to cover all alternatives, modifications, and equivalents as may be included within the spirit and scope of the various embodiments and equivalents set forth. For a general understanding, reference is made to the drawings. In the drawings, like references have been used throughout to designate identical or similar elements. It is also noted that the drawings may not have been drawn to scale and that certain regions may have been purposely drawn disproportionately so that the features and aspects could be properly depicted.

DETAILED DESCRIPTION

As used herein the term "oil" is intended to refer to a class of thick, viscous, typically flammable fluids or liquids that are generally insoluble in water but soluble in organic solvents, and include, for example, any of a group of natural esters of glycerol and various fatty acids, which are liquid at room temperature. Oils may be employed as lubricating and non-lubricating fluids (e.g., oils and emulsions thereof, cutting fluids and coolants, transformer oils and dielectric coolants, etc.)

As will be described in more detail below, in configurations when oil reference and measurement electrodes are present and air reference electrodes are not present, oil level determination is ratiometric for a low-level warning and absolute for a case when no oil is present on either electrode pair. Ratiometric measurements are preferred since it eliminates the effects of temperature, oil-type, oil condition, etc. on the oil's electrical properties. However, if no oil is present on either electrode only the effects of temperature remain, which can be readily compensated for if the sensor/oil temperature is measured. The absolute monitoring for presence/absence of oil considers the capacitance of both the oil reference and measurement electrode elements while the ratio of the two allow a determination of level. Therefore, a successful sensor design will have repeatable and significant-enough changes in capacitance such that absolute measurements are correct across all operational temperature ranges and oil-types.

Another embodiment of the disclosed sensor employs a third sensing element, an air reference electrode, to eliminate the need for any absolute measurements and leverage the more robust ratiometric measurements. In this embodiment, ratiometric measurements are simultaneously performed between the capacitance of both the oil reference electrode versus the air reference electrode and the measurement electrode versus the oil reference electrode. In this scenario, the ratio of the two oil-exposed electrodes can be leveraged to determine oil level, while the ratio of the two reference measurements can be used to determine if oil has dropped below the top of the oil reference electrode.

Referring to the embodiments of FIGS. 1A-1C and 2, in order to monitor fluid level, two or more sets of electrode pairs are used in the sensor system 110 employed within an oil reservoir or sump 114 on a piece of machinery or equipment. The oil sensing electrodes are arranged on a sensor 112 (e.g., 112A-112C of FIGS. 1A-1C, respectively) such that at least one measurement electrode pair 120 is placed at or across a range of interest (range of oil levels 132) while at least one other electrode pair/set 130 (e.g., 130A-130C of FIGS. 1A-1C, respectively) is placed at a position intended to stay submerged in all but the most severe low oil condition. For example, in FIG. 2, the range 132 may span between a low-oil warning level 140 and a full or desired level 144. Moreover, the range of oil levels are what one may see in a typical oil level sight glass 150. Also contemplated is an embodiment of the disclosed sensor that may be integrated with or within the sight glass 150 in order to facilitate installation of the disclosed sensor on pre-existing machinery.

Figures 1A, 1B:
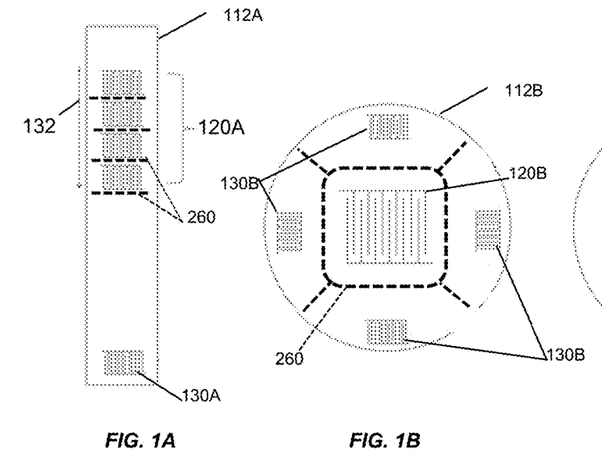
FIGS. 1A-1C are exemplary illustrations of the arrangement of reference and measurement electrodes in accordance with several alternative embodiments for the disclosed sensor.
Figure 1C:
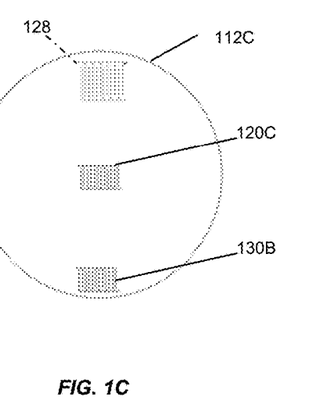

Further noted relative to FIGS. 1A-1C, the oil-sensing reference and measurement electrodes are pairs, or other multiples, of interdigitated electrodes. In one embodiment, the interdigitated electrodes are formed of copper, silver, aluminum or similar conductive materials, placed upon a non-conductive surface. Such electrodes may be produced, for example, through patterned etching of a multi-layer circuit board, for example, with one or more conductive layers sandwiched between non-conductive or insulating layers. Once formed, the interdigitated sensing elements 120, 130 are coated or covered in a non-conductive material that prevents current flow from one electrode to the other. Use of a coating helps repeatability in measuring capacitance since the coating eliminates the possibility of electrical shorting of electrodes from metallic debris or other contaminants. The electrode coating also prevents aging of the electrode material through corrosion or other mechanisms such as abrasion. Due to the limited depth of field of the sensing electrodes, the thickness of the coating must be minimized in order to maximize the sensitivity of the sensing electrodes. Coating thicknesses of up to 100 μm, and more specifically thicknesses in the range of 5 nm to about 100 μm, are contemplated and the thickness employed may be a function of the coating material(s), which can include epoxy coating, insulating films, electrode anodization, or other insulating methods.

In one embodiment of the sensor, the electrode coating exhibits oleophobic and hydrophobic properties. By using an oleophobic coating, the response time of the system is dramatically improved by minimizing the time required for oil to dissipate from the surface of the electrodes. This provides benefit to applications in which a drop in oil level must be detected quickly as well as applications which produce a high degree of sloshing and foaming in the region of the sensor. The hydrophobic properties prevent moisture absorption near the capacitive relative humidity (RH) sensor, which is known to skew results. It will be further appreciated that reference herein to a relative humidity (RH) sensor include what is commonly described as a water activity sensor when referring to the sensing and measurement of water in oil.

Figure 2:
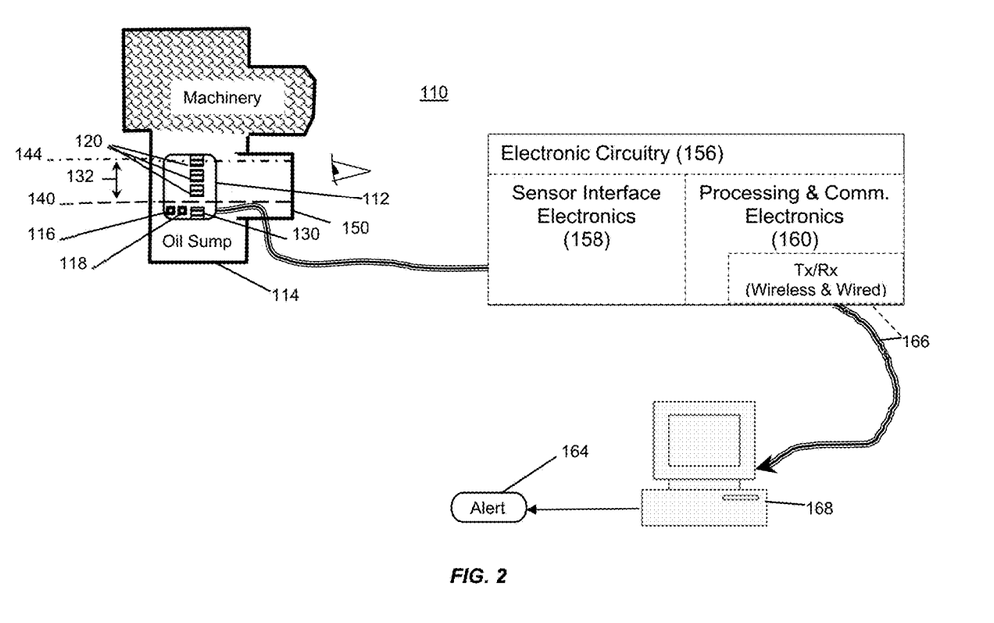
FIG. 2 is a schematic block diagram illustrating various components of the disclosed sensor.

As will be further appreciated, the signals produced from sensor 112, which may also include temperature signals from sensor element 116 and a water contamination sensor 118, are passed to electrical circuitry 156. Circuitry 156 may include a sensor interface electronics section 158 and a processing and communications electronics section 160, which may include a microcontroller (μC) 162 or similar programmable device(s) for the collection, storage and processing of signals to/from the circuitry, including at least preliminary interrogation of such signals for the detection of a low-oil condition. It will be further appreciated that some or all of the circuitry and/or functionality facilitated by the electronic circuitry may be provided by one or more integrated circuits designed with the features described herein. Moreover, raw signal data, processed signal data and/or level warnings and the like may be stored in a memory on the integrated circuit or an associate memory device, or passed via a wired (or wireless) communication channel 166 to a workstation 168 or similar computing device suitable for tracking the oil level and/or initiating an alert 164 in the event a low oil level is detected by sensor 112. Examples of alert outputs that may be generated by the disclosed sensing system include: audible, visual, e-mail message, text (SMS) message, telephone, as well as wired or wireless communications of sensor measurements and status to a host system, etc.

Several configurations for the arrangement of the sensors, 112A-112C respectively, are depicted in FIGS. 1A-1C. FIG.

1A represents a configuration where multiple measurement electrodes 120A are used, over measurement range 132, in comparison with a single reference electrode 130A. FIG. 1B represents a sensor configuration where only one measurement electrode 120B is used in comparison to one or more reference electrodes 130B, where the reference electrodes 130B are arranged in a regular pattern (e.g., one per quadrant) about the measurement electrodes 120B at the center. This configuration allows for flexibility in installation orientation to eliminate the need for a specific orientation of sensor 112B during installation. FIG. 1C represents a single reference electrode pair 128 and a single measurement electrode pair 120C. In each of the illustrated sensor configurations 112A-112C, the range of useful measurements is controlled by the placement and sizing of the measurement electrode. It is recognized that optimal performance for a given application may require further variants of these designs. Furthermore, represented in FIG. 1C is the placement of the optional air reference electrode 128, which must be placed in a position that will not be exposed to oil.

As will be appreciated, all measurement electrode signal readings are intended to be performed for comparison with the reference electrode signal readings. When oil is covering both reference (130) and measurement (120) electrodes, their dielectric readings will be the same, regardless of oil temperature or contaminations. As the oil level in the sump decreases, oil recedes from the surface of the measurement electrodes 120, and the dielectric signal response observed from the measurement electrodes will drop below that of the reference electrode 130 indicating a drop in oil level below that of the particular measurement electrode(s). The result can be interpreted as either a binary state (normal vs low oil) by thresholding the ratio or as a measurement of oil level across the measurement electrode's measurement range. By comparing the ratio of dielectric signals between the measurement and the reference electrodes, the effects of temperature and contamination are removed, resulting in a measurement which is proportional to oil level. In the scenarios without the optional air reference electrode 128, the oil reference electrode is also used in a binary sense—oil present or not present—and requires a priori knowledge of the electrode's output under non-wetted conditions. As depicted in the embodiment of FIG. 2, a second sensing device, a temperature sensor 116, may be placed near the reference electrode to allow for the sensor system's compensation of thermal effects relative to the dielectric signals. This is necessary for the accurate detection of an un-wetted reference electrode when an air reference electrode is not present. The temperature correction of the dielectric measurement is accomplished by establishing a temperature versus dielectric relationship for an un-wetted electrode and using this relationship to compensate future measurements to a specific temperature. In one embodiment, the temperature sensor 116 may be in the form of a thermistor, a thermocouple, or a resistance temperature detector (RTD).

In one embodiment of the sensor interface electronics, the capacitance of the electrodes is used to control the frequency of a specially designed square wave generator. The associated electronic circuitry 158 outputs this square wave. And, since counters/timers are commonly integrated on modern microcontrollers, the frequency of oscillation can be easily determined using a purely digital system. A simple program can be employed that routinely reports the oscillation frequency, and from the reported frequency, and the ratiometric comparison between the measurement and reference electrodes, the oil-level.

In another embodiment of the sensor interface electronics, the capacitance of the electrodes is used to control the discharge of a known voltage through a known impedance. The duration of the discharge is measured and compared to that of a reference capacitor. With these values, the discharge time can be used to calculate the capacitance of the electrodes. The interface electronics 158 are capable of charging the electrodes and measuring the discharge times. The discharge times are compared in a ratiometric calculation to derive the capacitance, which is handled by the same interface electronics device. The device outputs the results digitally to the workstation 168.

A third sensing element, referred to as a relative humidity (RH) sensor 118, which may be integrated in the disclosed sensing device is another capacitive sensing element designed for characterizing the amount of water contamination in the oil. In one embodiment, these devices operate by placing a hygroscopic material between two electrodes of a capacitor. As the hygroscopic material absorbs and desorbs water the dielectric constant of the material changes and, accordingly, the capacitance of the device increase and decreases. In order to compensate this device for the effects of temperature, output of the previously described temperature sensing element can be used. The temperature correction of the relative humidity (RH) reading is accomplished through a priori knowledge of the RH sensor's temperature sensitivity. In one embodiment, the RH sensor 118 may be made from a hygroscopic dielectric material between a pair of electrodes. Alternative implementations exist, such as resistive humidity sensors, that may also be used.

Figure 3:
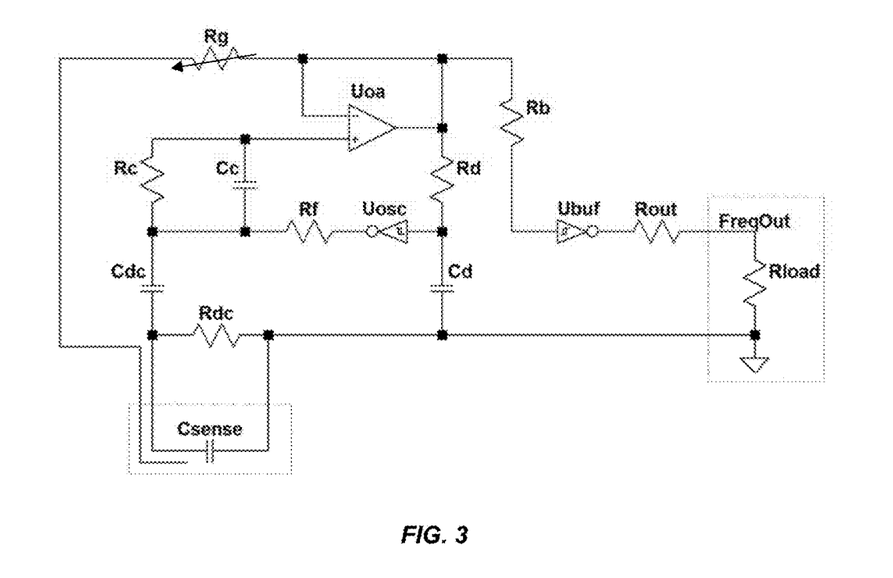
FIG. 3 is an exemplary circuit diagram for use with the disclosed sensor (e.g., reference and measurement electrodes)

Having described the basic components of the sensing system, and the various sensors, attention is now turned to the electronic circuitry that may be employed in implementing an embodiment of the sensing system. FIG. 3 is an illustration of an electrical schematic diagram depicting some components of the electronic circuitry 156 that may be employed for the sensing system 110. A square wave oscillator designed to have low cost, high input impedance, low supply-current draw, stability/reliability, and an operational bandwidth that maximizes performance, is preferred for the disclosed embodiments. For example, a high oscillator input impedance means a smaller parasitic capacitance is seen by the oscillator, which causes an increase in the percent-change in output frequency for different oil-levels. The design uses an operational amplifier ($U_{oa}$) to buffer and guard the electrode's signal from the sensor ($C_{sense}$) before the signal is used to control the frequency of oscillation. A filter circuit was designed to be placed in series between the non-inverting input and the sensing line. The filter (e.g., FIG. 3, 174) was designed to decrease the effect of the non-inverting input's capacitance on the buffer's transfer function. Details of the design are further described below.

Since the buffer circuit outputs a low-impedance signal with the same voltage as the sensing electrodes, it is also used to drive a capacitive guard that surrounds the high-impedance-signal's cable connection to the sensor (see e.g., Rg). Since the cable's parasitic capacitance increases with voltage differential between the cable and its surface, forcing the voltage at the surface of the conductor to be identical to the conductor's voltage ideally eliminates any capacitance introduced by the cables.

Figure 4:
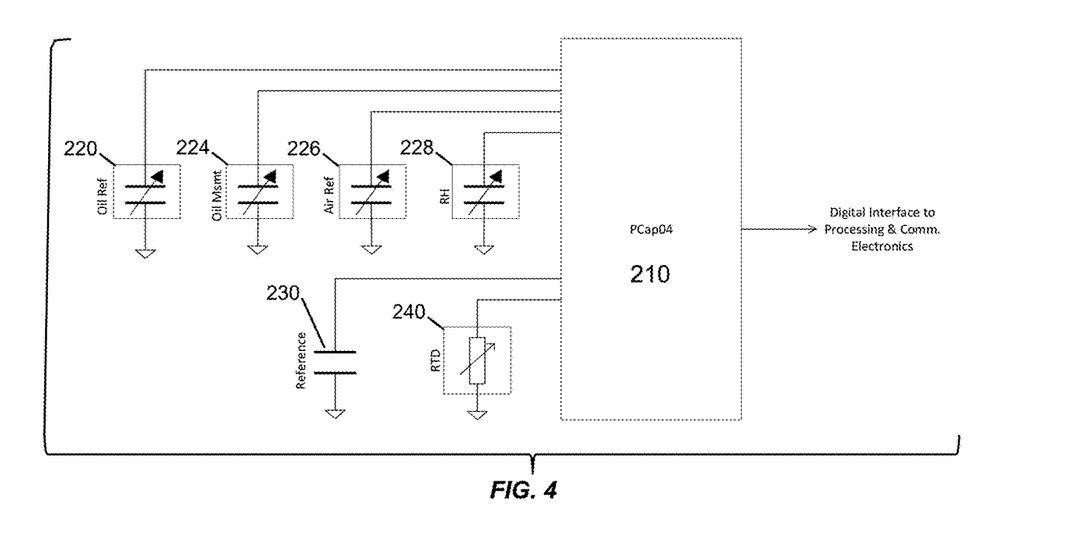
FIG. 4 illustrates an alternative embodiment employing an integrated circuit for converting time measurements to capacitive values.

An alternative embodiment utilizes an integrated circuit for converting time measurements to capacitive values. An electrical schematic of this embodiment is shown in FIG. 4. The illustrated embodiment uses an integrated circuit 210, for example, a PCap04 IC produced by AMS AG, although similar capacitance-to-digital integrated circuits are also considered. Note that the schematic shown is intentionally reduced in complexity for illustrative purposes. The integrated circuit implementation allows for a minimal component count design and provides integrated measurement, processing, and digital communication capabilities. The design uses time-to-capacitance conversions based on the principle $$\frac{\tau_x}{\tau_{ref}} = \frac{C_x}{C_{ref}}, \qquad \text{Eq. 1}$$

where $\tau_x$ is the discharge time constant of the sensor, $\tau_{ref}$ is the discharge time constant of the reference circuit, and $C_x$ and $C_{ref}$ are the calculated capacitances. The discharge time constant is defined as $$\tau = k \times R \times C, \qquad \text{Eq. 2}$$

where R is the discharge resistance and k is a constant. In this implementation, one integrated circuit can perform capacitance-to-digital conversions for the oil reference interdigitated electrode 220, oil measurement interdigitated electrode 224, and air reference interdigitated electrodes 226 in addition to a high precision reference capacitor measurement 230, and a RTD-style temperature sensor 240. Thereby enabling a minimal electronics solution for the described multi-sensor embodiment.

The device also drives a capacitive guard that surrounds the interdigitated electrodes, as well as the traces to the capacitive RH sensor 228. This reduces parasitic capacitances that would otherwise degrade the sensitivity of the device.

In either of the described electronics interfaces, the RH sensor circuit works on the same principle as the level sensing circuit—with the same electronics applicable to measuring the capacitance of the RH sensor. In either implementation, the functional similarity between oil-level and RH determination is convenient in that it allows for a multi-package integrated circuit to be used instead of separate discrete circuitry for both. Consolidating as much functionality to single integrated circuits permits further savings on production cost and circuit-size.

A primary advantage of the described circuits is the extremely low power consumption required to obtain measurements. As both the RH sensing and level sensing elements have capacitance values in the picofarad range, change/discharge cycles only consume picojoules of energy. Additionally, the measurements can be acquired in a fraction of a second. When combined, these features result in a methodology well suited for use in battery powered or energy harvester-based designs, and may employ a stored energy source such as a storage capacitor or battery (e.g., battery holder 250, FIG. 11).

One embodiment of the sensor considers the use of a thermal or vibration-based energy harvester in order to provide power to the device. For many oil-level monitoring applications, the oil temperature will be significantly higher than that of the surrounding air. Pumps and gearboxes, for example, often have oil temperatures around 60° C. while surrounding temperatures will be at or near normal ambient temperatures. This temperature gradient, in combination with the low power electronics, provides the opportunity to use a thermal electric generator to power the design. Alternatively, these applications also often have fixed rotating speeds, resulting in a predictable vibration frequency and allowing for a frequency-optimized vibration-based energy harvester. In combination with the energy harvesting device, a battery and/or super-capacitor can be used to power the device during low temperature, low-vibration, or start-up conditions.

Figure 5:
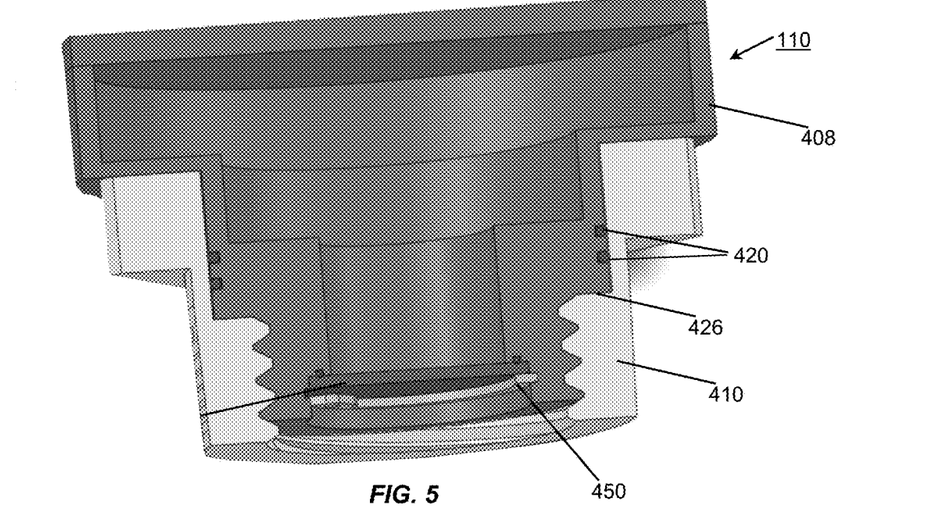
FIGS. 5-6 illustrate cutaway views of a sensing module in accordance with embodiments installed in bushing.
Figure 6:
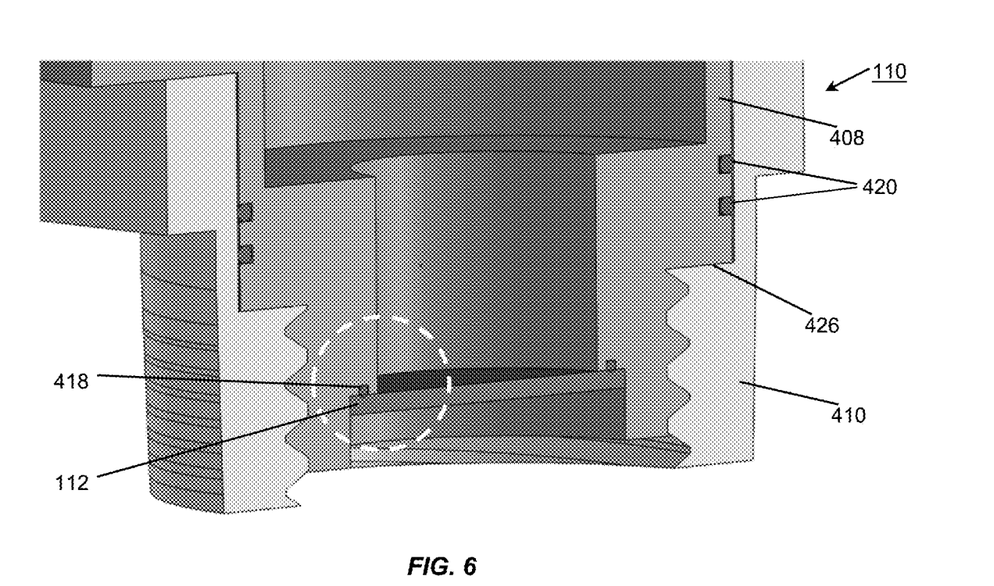

Mechanical Considerations:

Referring next to FIGS. 5-6, which are cutaway views of the sensing module 110 in a housing 408 installed in a bushing 410, where the sensor assembly consists of two major components. First, a bushing (410) to thread into a sight glass port on the asset to be monitored. This bushing utilizes exterior threads that match the assets threads or flange and has a set of wrench flats or spanner groves/holes for an installation tool to engage onto. A range of fluid ports are considered including NPT, BSPP, Flange, etc. In all cases, the bushing 410 will need to be installed onto the unit until a leak proof seal is achieved. The number of rotations and final radial position to achieve this is unknown. For some embodiments of this sensor, that is unacceptable so a method to orient the sensor while maintaining a seal is needed.

Next, the interior geometry of the bushing is such that the sensing module assembly 110, possibly containing the sensing head PCB, processing electronics, batteries, etc., can be threaded into the bushing 410. As these threads engage and pull the sensing module into the bushing, one or several O-rings 420 (depending on pressure requirements) begin to engage on a cylindrical sealing surface inside the bushing. During installation, it is expected that the sensing module will be threaded clockwise until it bottoms out on the stepped surface 426 between the threads and O-rings. Once the module has bottomed out, the user will turn the module counterclockwise until sensor's orientation is such that the sensor is aligned to the gravity vector (identified by arrows or lines on the sensing modules cover). This ensures that the sensor's elements are aligned with the plane of the oil level. Because the O-rings are set at a depth into the outer bushing deeper than 1 pitch distance of the lead screw, the user will have at least 360 degrees of rotation available to align the sensor, while maintaining a proper seal on the assembly.

The friction of the O-rings in the bore will retain the radial orientation of the sensor module during operation. In higher vibration environments, a set screw or tie down (not shown) can be added to the module to lock rotation relative to the outer bushing, or interference thread fits can be utilized.

The bore O-rings 420, in combination with the PCB sensing element 112, its O-ring 418, and the sensing module housing 408 provide a completely sealed assembly while allowing the proper radial orientation of the sensing element.

A single sensing module design can serve multiple asset ports through the use of different bushings 410. These bushing would have the same internal geometry to mate with the sensor module, yet utilize varying thread profiles, wall thicknesses, etc. to mate with a wide variety of port configurations.

Figure 7:
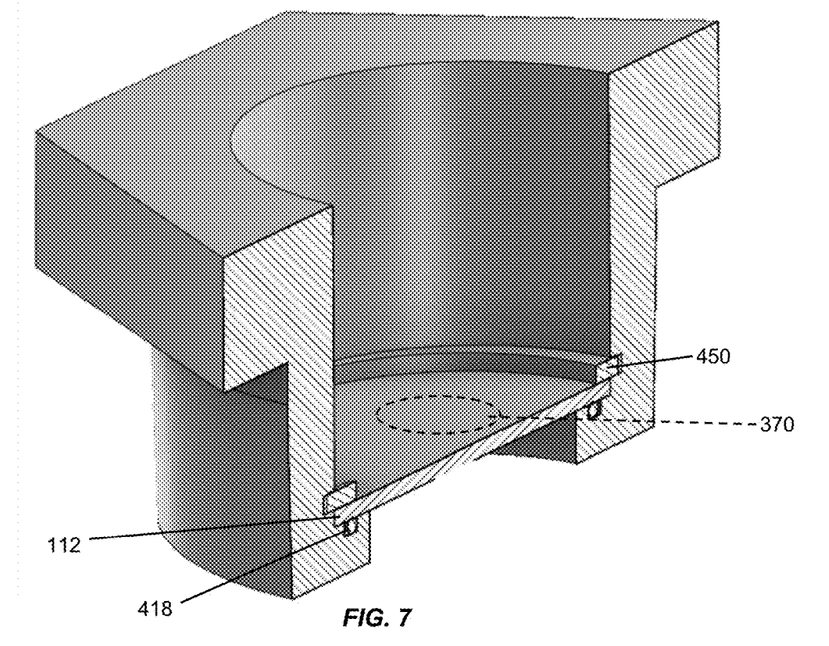
FIGS. 7-8 illustrate cutaway views of an embodiment of a sensor printed circuit board (PCB) sealed or installed directly in a bushing.
Figure 8:
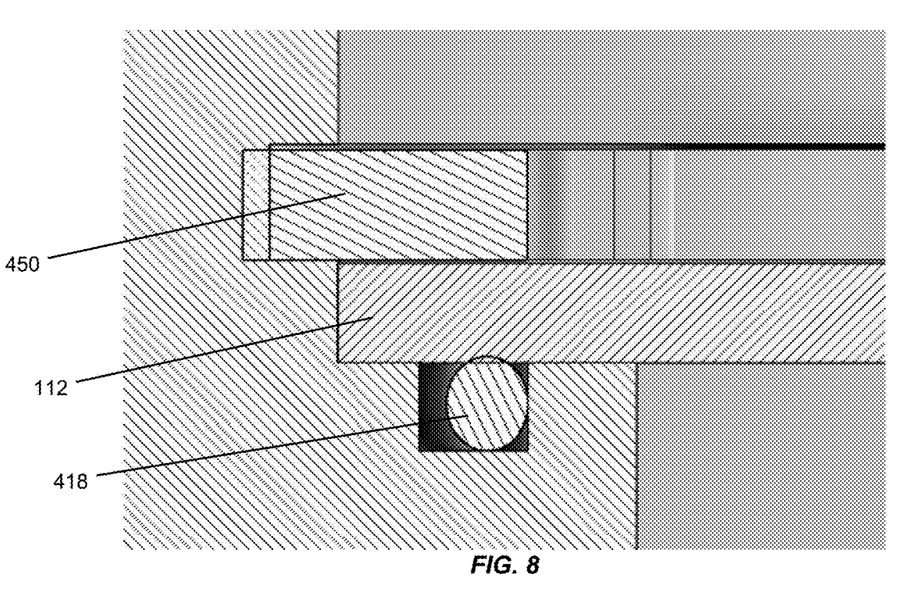

Printed circuit board sensing module 112 can be retained during manufacturing via either over-molded plastic, a snap ring 450 post molding, a solvent adhesive, ultrasonic welding, or other retention mechanism. The O-ring 418 may be optional if over-molding is utilized for PCB retention depending on the system pressure. The sensing element can also be retained into the bushing itself in cases where its proper radial indexing can be assured. The processing electronics, batteries (if required), and cables can be installed into the back of the housing/bushing. An example of this embodiment is shown in FIGS. 7-8. In one embodiment the printed circuit board sensing module 112 may be formed using a substrate including a conventional FR4-type material, or a specific glass or ceramic (e.g., Aluminum-based ceramics) material may be employed for the substrate. The use of the Al-based substrate materials provides improved chemical and temperature resistance, as well as to provide lower rates of water absorption by the substrate, which in turn results in improved reliability of the sensor by reducing or eliminating the impact of water on the substrate.

As will be appreciated there may be design considerations that are important when utilizing PCB 112 as part of the pressure vessel for both sensing module and bushing installation. More specifically, it will be necessary to assure that blind, buried or filled vias are employed to maintain pressurization from one side of PCB to another. In other words, there should be no open vias exposed to the pressurized surface, and inter-layer transitions should be located outside of the pressurized area. Such design considerations result in minimal, if any, through hole parts, especially in the pressurized area of the PCB.

Figure 9:
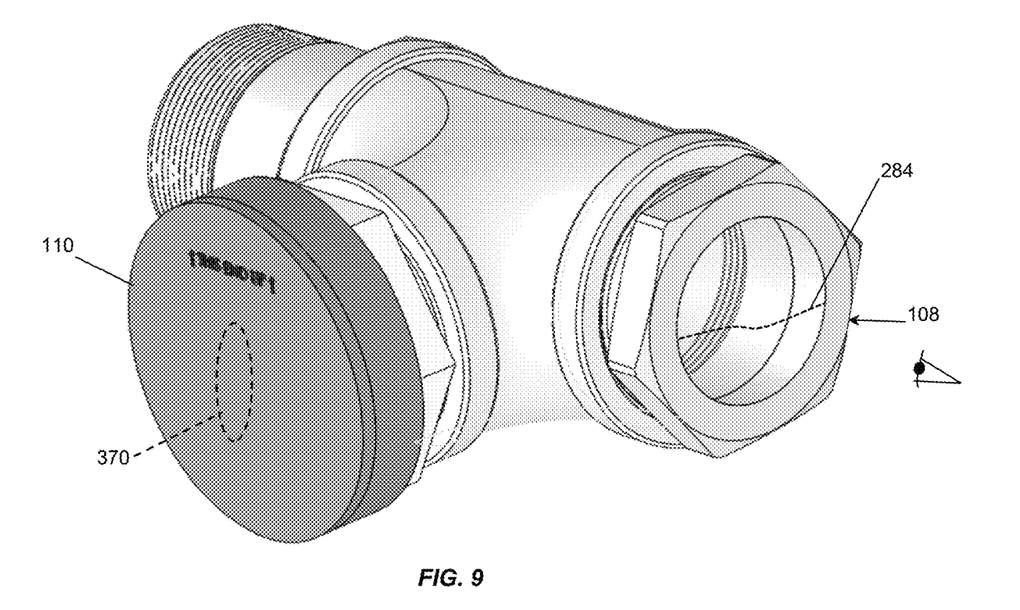
FIG. 9 is an illustration of a method of installation in a Tee fitting for maintaining sight glass functionality.
Figure 10:
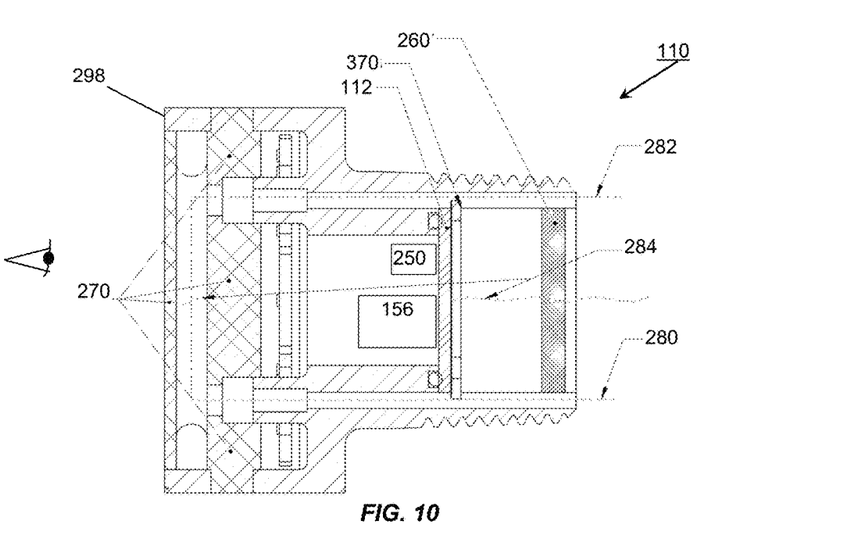
FIGS. 10-11 are illustrations of a complete sensor in a clear housing in accordance with an embodiment.
Figure 11:
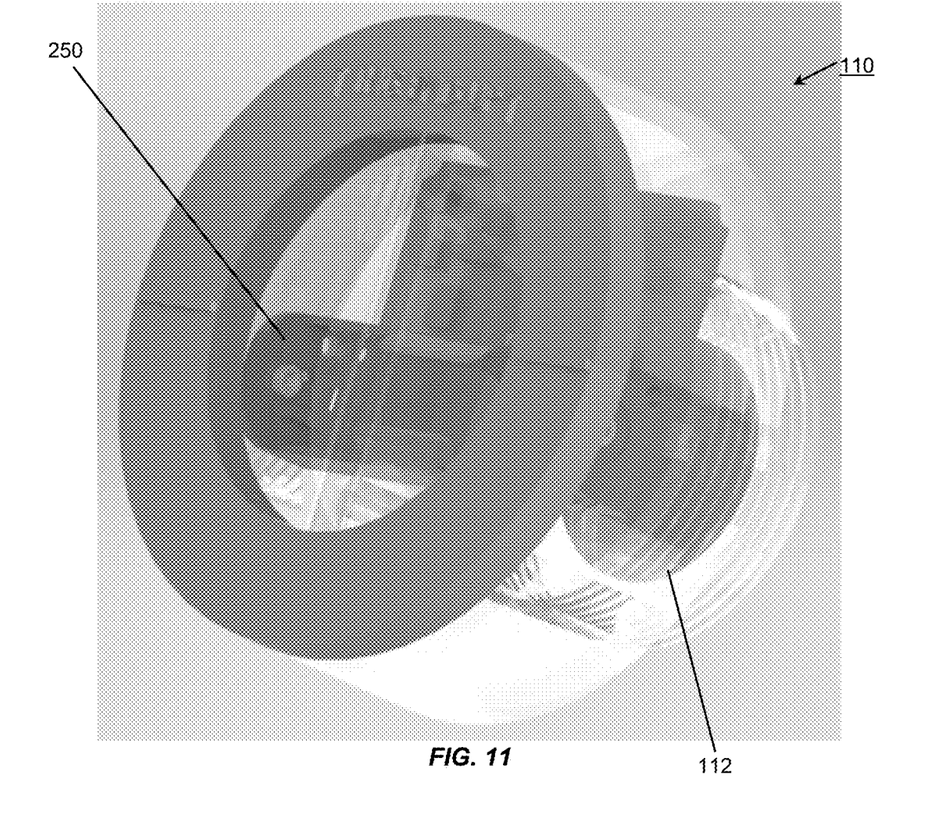

Referring to FIGS. 9-11, alternative methods to retain visual sight glass functionality include:

A) Tee Fitting Installation (FIG. 9)
 Allows use of a standard sight glass assembly 108.
 Orients the sensing assembly 110 perpendicular to the original sight glass port 108 in the same plane of oil.
 Oil will flow to both the sensor and sight glass retaining the existing visual interface a user may be accustomed to.

B) Display LED(s) may also be incorporated into region 370 on the back surface of the PCB or another component, for example the outer cover as represented in FIG. 9, so as to be viewable by a user
 Virtual sight glass using bar graph LEDs 370 to mimic the actual system oil level
 Individual LED(s) showing state or color changes based on system oil level C) Connectivity Methods
 Wireless over a variety of protocols
 Wired via over-molded cable, cord grip, or connectors installed in the sensor housing(s).

D) Clear or Transparent Housing Style, for example as depicted in FIGS. 10-11
 Clear acrylic (or other oil resistant clear plastic to be determined) areas 270 function as both the housing for the sensor element and electronics, along with providing a sight-glass for an oil flow path 280 connected to air vent path 282 for the oil level 284 to be visible on the front of the housing for sensor 110.
 All the electronics can be over-molded and sealed into the lower threaded enclosure.
 The sealing ring 298 can be solvent or ultrasonically welded into place afterwards creating a sealed loop for the oil display on the front (outermost) face of the complete assembly.
 This results in a low-cost, two-piece assembly with minimal labor to construct.

In one embodiment of the sensor, a porous baffle material 260 (e.g., FIGS. 1A, 1B, 10) is used, over, between and/or around measurement electrodes and other sensor elements to limit or dampen the effects of oil sloshing on the face of the sensing element and to prevent oil foaming from impacting level measurements. In this embodiment sensor response time is inversely proportional to the porosity of the baffle and can be optimized to the application. The baffle(s) may be formed from porous plastics, metals, and/or ceramics, as well as stamped or folded sheet material such as sheet metal, plastic baffles, composites. And, the baffle structures may include louvers, holes, etc. so as to provide labyrinth type structure tailored to manage or control for typical system fluid motion, viscosity, and other characteristics such as foaming.

It should be understood that various changes and modifications to the embodiments described herein will be apparent to those skilled in the art. Such changes and modifications can be made without departing from the spirit and scope of the present disclosure and without diminishing its intended advantages. It is therefore anticipated that all such changes and modifications be covered by the instant application.

What is claimed is:

1. A fluid monitoring sensor for installation within an equipment port, comprising:
 at least a first pair of interdigitated reference electrodes, said reference electrodes placed at a position normally submerged in fluid in all but a severe low-fluid condition;
 at least one pair of interdigitated measurement electrodes, said at least one pair of measurement electrodes being separated and spaced apart from said reference electrodes and from one another, so as to enable the monitoring of fluid at one or more levels;
 electronic circuitry, operatively connected to both the reference electrodes and the measurement electrodes, for applying charges to the reference electrodes and the measurement electrodes;
 a temperature sensor, located in proximity to said reference electrodes;
 a water sensor suitable for characterizing the amount of water present in the fluid, said water sensor employing a capacitive sensing element with a hygroscopic material between two electrodes of a capacitor, such that the dielectric constant of the material, as measured by the capacitance, changes as a function of the amount of water absorbed by the hygroscopic material, thereby producing a signal indicative of a relative level of water in the fluid,
 wherein said interdigitated reference electrodes, interdigitated measurement electrodes, electronic circuitry, temperature sensor and water sensor are located on a single printed circuit board within a sensing module assembly that is threadedly connected to the port, the single printed circuit board being positioned perpendicular to a plane of a fluid level being sensed, and wherein an orientation of the sensing module assembly is rotationally adjustable relative to the port to ensure that at least some elements on the printed circuit board are aligned with the plane of the fluid level being sensed; and
 a programmable device for the collection, storage and processing of signals to and from said electronic circuitry, said temperature sensor and said water sensor and for at least preliminary interrogation of such signals for the detection of at least one fluid condition.

2. The fluid monitoring sensor according to claim 1, wherein the at least one fluid condition is selected from the group consisting of: fluid level; fluid temperature; water contamination in the fluid; and dielectric condition of the fluid.

3. The fluid monitoring sensor according to claim 2, where the fluid consists essentially of oil.

4. The fluid monitoring sensor according to claim 1, wherein said electronic circuitry further includes sensor interface electronics for the reference electrodes, measurement electrodes, temperature sensor, water sensor and processing and communication electronics.

5. The fluid monitoring sensor according to claim 4, wherein said sensor interface electronics further includes a buffer circuit that drives a capacitive guard that reduces or substantially eliminates capacitance introduced by cables employed between the sensor and the sensor interface electronics.

6. The fluid monitoring sensor according to claim 1, wherein said reference electrodes are arranged in a regular pattern about the measurement electrodes.

7. The fluid monitoring sensor according to claim 1, further including at least one pair of interdigitated air reference electrodes.

8. The fluid monitoring sensor according to claim 7, wherein said air reference electrodes are placed at a position normally exposed to air.

9. The fluid monitoring sensor according to claim 1, further including a lock against rotation of the sensing module assembly therein, preventing a further change in the radial orientation of the sensing module assembly.

10. The fluid monitoring sensor according to claim 9, wherein said printed circuit board is operatively associated with a bushing, said printed circuit board including a substrate material exhibiting chemical and temperature resistance, and a low rate of water absorption.

11. The fluid monitoring sensor according to claim 10, wherein the sensing module assembly further includes an enclosure for said programmable device and a source of power.

12. The fluid monitoring sensor according to claim 9 where at least one surface of the printed circuit board further provides a sealing surface for a fluid-to-air seal.

13. The fluid monitoring sensor according to claim 12 where said fluid-to-air seal is accomplished, at least in part, using at least one O-ring in contact with the printed circuit board, said at least one O-ring applying pressure to the surface of the printed circuit board, preventing a further change in the radial orientation of the sensing module assembly.

14. The fluid monitoring sensor according to claim 13 where said printed circuit board includes a substrate including an Aluminum-based ceramic.

15. The fluid monitoring sensor according to claim 9 further including a porous baffle material.

16. The fluid monitoring sensor according to claim 1 wherein an oliophobic and hydrophobic coating is employed over at least the reference and measurement electrodes.

17. The fluid monitoring sensor according to claim 1 wherein external energy is harvested to provide power to the fluid monitoring sensor.

18. The fluid monitoring sensor according to claim 17 where the external energy is harvested using a device selected from the group consisting of a thermal electric generator and a vibration-based energy harvester.

19. The fluid monitoring sensor according to claim 1 wherein said electronic circuitry employs low power electronics to enable sensor operation and wireless communication with the sensor to be powered using a stored energy source.

20. The fluid monitoring sensor according to claim 1 further including LEDs to provide a visual indication of the sensed fluid level.

21. The fluid monitoring sensor according to claim 1, wherein the sensor is operatively associated with a transparent housing in order to provide an observer with a view of the fluid level being sensed.

22. The fluid monitoring sensor according to claim 1, wherein the sensor is suitable as a replacement for an existing fluid-level sight glass.

23. An equipment oil monitoring system, comprising:
an oil level sensor, formed on a face of a printed circuit board, said oil level sensor including at least a first pair of interdigitated reference electrodes, said reference electrodes placed at a position normally submerged in fluid in all but a severe low-oil condition, at least one pair of interdigitated measurement electrodes, said at least one pair of measurement electrodes being separated and spaced apart from said reference electrodes and from one another, so as to enable the monitoring of oil at one or more levels, and
electronic circuitry, operatively connected to both the reference electrodes and the measurement electrodes, for applying charges to the reference electrodes and the measurement electrodes;
a temperature sensor, located in proximity to said reference electrodes;
a water sensor suitable for characterizing the amount of water present in the oil, said water sensor employing a capacitive sensing element with a hygroscopic material between two electrodes of a capacitor, such that the dielectric constant of the material, as measured by the capacitance, changes as a function of the amount of water absorbed by the hygroscopic material, thereby producing a signal indicative of a relative level of water in the oil;
said electronic circuitry further includes sensor interface electronics for the reference electrodes, measurement electrodes, temperature sensor, water sensor and processing and communication electronics; and
a programmable device for the collection, storage and processing of signals to and from said electronic circuitry, said temperature sensor and said water sensor and for at least preliminary interrogation of such signals for the detection of at least one oil condition selected from the group consisting of: oil level, oil temperature, water contamination in the oil, and dielectric condition of the oil;
wherein said oil level sensor, temperature sensor, water sensor, electronic circuitry and programmable device are located on the single printed circuit board within a sensing module assembly that is enclosed along with a source of power, the single printed circuit board being positioned perpendicular to a plane of the oil level being sensed, and
wherein an orientation of the sensing module assembly is rotationally adjustable relative to a port on the equipment, to ensure that at least some elements on the printed circuit board are suitably oriented with the plane of the oil level being sensed.

24. A fluid monitoring system, comprising:
a fluid level sensor, formed on a first face of a printed circuit board, said fluid level sensor including
at least a first pair of interdigitated reference electrodes, said reference electrodes placed at a position normally submerged in the fluid in all but a severe low-fluid condition, and
at least one pair of interdigitated measurement electrodes, said at least one pair of measurement electrodes being separated and spaced apart from said reference electrodes and from one another, so as to enable the monitoring of the fluid at one or more levels;

a temperature sensor, located on the first face of the printed circuit board in proximity to said reference electrodes;

a water sensor suitable for characterizing the amount of water present in the fluid, said water sensor employing a capacitive sensing element with a hygroscopic material between two electrodes of a capacitor, such that the dielectric constant of the material, as measured by the capacitance, changes as a function of the amount of water absorbed by the hygroscopic material, thereby producing a signal indicative of a relative level of water in the fluid;

at least one pair of interdigitated air reference electrodes at a position exposed to air;

electronic circuitry, operatively connected to both the reference electrodes and the measurement electrodes of the fluid level sensor and to the air reference electrodes, for applying charges to the reference electrodes, the measurement electrodes and the air reference electrodes;

said electronic circuitry further including sensor interface electronics for the reference electrodes and measurement electrodes of the fluid sensor, temperature sensor, water sensor and air reference electrode and processing and communication electronics;

wherein said sensor interface electronics further include at least one buffer circuit that drives a capacitive guard to reduce or substantially eliminates capacitance introduced by cables employed between one or more of the fluid sensor, the temperature sensor, the water sensor and the air reference electrodes, and the sensor interface electronics;

a programmable device for the collection, storage and processing of signals to and from said electronic circuitry, said fluid sensor, said temperature sensor, said water sensor, and said air reference electrodes and for at least preliminary interrogation of such signals for the detection of at least one fluid condition selected from the group consisting of: fluid level, fluid temperature, water contamination in the fluid, and dielectric condition of the fluid; and wherein said fluid level sensor, temperature sensor, water sensor and air reference electrodes are positioned on the first face of the printed circuit board that is exposed to the fluid via a port and said electronic circuitry and programmable device are operatively affixed on a second face of the printed circuit board separated from the fluid, and where the printed circuit board is located within an enclosure along with a source of power, the single printed circuit board being perpendicular to a plane of the oil level being sensed, and wherein an orientation of the printed circuit board and enclosure is rotationally adjustable relative to the port to ensure that at least some elements on the printed circuit board are suitably oriented with the plane of the oil level being sensed.

* * * * *